(12) United States Patent
Alotaibi

(10) Patent No.: US 10,182,915 B2
(45) Date of Patent: Jan. 22, 2019

(54) CARTILAGE PROSTHETIC IMPLANT

(71) Applicants: NATIONAL GUARD HEALTH AFFAIRS, Riyadh (SA); KING SAUD BIN ABDULAZIZ UNIVERSITY FOR HEALTH SCIENCES, Riyadh (SA); KING ABDULLAH INTERNATIONAL MEDICAL RESEARCH CENTER, Riyadh (SA)

(72) Inventor: Abdullah Muhayl Alotaibi, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 0 days.

(21) Appl. No.: 15/117,498

(22) PCT Filed: Dec. 24, 2015

(86) PCT No.: PCT/IB2015/002600
§ 371 (c)(1),
(2) Date: Aug. 9, 2016

(87) PCT Pub. No.: WO2016/067115
PCT Pub. Date: May 6, 2016

(65) Prior Publication Data
US 2016/0367369 A1 Dec. 22, 2016

(30) Foreign Application Priority Data
Oct. 26, 2014 (SA) .................. 114360001

(51) Int. Cl.
A61F 2/08 (2006.01)
A61F 2/30 (2006.01)
A61F 2/38 (2006.01)

(52) U.S. Cl.
CPC .......... *A61F 2/30756* (2013.01); *A61F 2/389* (2013.01); *A61F 2/3859* (2013.01); *A61F 2/3872* (2013.01); *A61F 2002/30757* (2013.01)

(58) Field of Classification Search
CPC .. A61F 2/30756; A61F 2/3872; A61F 2/3859; A61F 2/389; A61F 2002/30757
See application file for complete search history.

(56) References Cited

U.S. PATENT DOCUMENTS

| 4,502,161 A * | 3/1985 | Wall .................... A61F 2/30756 606/286 |
| 6,132,468 A | 10/2000 | Mansmann |

(Continued)

FOREIGN PATENT DOCUMENTS

| DE | 25 01 080 A1 | 7/1976 |
| EP | 1 265 560 B1 | 11/2012 |

(Continued)

OTHER PUBLICATIONS

International Search Report and Written Opinion of the International Searching Authority dated May 6, 2016 in PCT/IB2015/002600 Filed Dec. 24, 2015.

*Primary Examiner* — Brian Dukert
(74) *Attorney, Agent, or Firm* — Oblon, McClelland, Maier & Neustadt, L.L.P.

(57) ABSTRACT

This disclosure relates to a cartilage prosthetic implant that can be used in orthopedics for a replacement of a damaged cartilage in a joint between opposing bones, for example in the case of osteoarthritis or trauma. The cartilage prosthetic implant described herein can replace the damaged cartilage at the joint without cutting bones of the joint. The cartilage (Continued)

prosthetic implant can maintain or restore a native joint anatomy, allowing for a natural movement at the joint. The cartilage prosthetic implant can be used as a permanent treatment or an intermediate treatment before requiring a total joint replacement. An example of the cartilage prosthetic implant is described for a knee joint replacement and is divided into a proximal implant configured to replace a cartilage at a distal end of a femur bone and a distal implant configured to replace a cartilage on a proximal end of a tibia bone.

6 Claims, 8 Drawing Sheets

(56) References Cited

U.S. PATENT DOCUMENTS

| | | | |
|---|---|---|---|
| 7,833,274 B2* | 11/2010 | Popoola | A61F 2/38 623/20.14 |
| 8,333,805 B2* | 12/2012 | Williams, III | A61F 2/36 623/20.35 |
| 8,617,242 B2* | 12/2013 | Philipp | A61F 2/30756 623/18.11 |
| 2005/0171604 A1 | 8/2005 | Michalow | |
| 2009/0187252 A1 | 7/2009 | Howald et al. | |
| 2011/0054631 A1 | 3/2011 | Ratron et al. | |
| 2011/0288642 A1* | 11/2011 | Forsell | A61F 2/3872 623/14.12 |
| 2015/0297350 A1* | 10/2015 | Robichaud | A61F 2/3859 623/20.32 |

FOREIGN PATENT DOCUMENTS

| | | |
|---|---|---|
| FR | 2 803 191 A1 | 7/2001 |
| WO | 2007/125060 A1 | 11/2007 |
| WO | 2009/115613 A1 | 9/2009 |

* cited by examiner

Anterior View    Lateral View

Posterior View (posterior view in the coronal plane)

(posterior view in the coronal plane)

(upper view in the horizontal plane)

CARTILAGE PROSTHETIC IMPLANT

CROSS REFERENCES TO RELATED APPLICATIONS

The present application contains subject matter disclosed in commonly owned Saudi application No. GC 114360001, filed Oct. 26, 2014, which is granted Sep. 1, 2015 as Saudi Patent No. 4307 at the Saudi Arabian General Directorate of Industrial Property Filing and Granting. The disclosures of the application referenced above is incorporated herein in its entirety by reference.

FIELD OF THE INVENTION

This disclosure relates to a prosthetic implant that can be used in orthopedics for a replacement of a cartilage in a joint.

SUMMARY

This disclosure relates to a cartilage prosthetic implant that can be used in orthopedics for a replacement of a damaged cartilage in a joint between opposing bones, for example in the case of osteoarthritis or trauma. The cartilage prosthetic implant described herein can replace the cartilage in the joint without cutting underlying bones of the joint. The cartilage prosthetic implant can maintain or restore a native joint anatomy, allowing for a natural movement at the joint. The cartilage prosthetic implant can be used as a permanent treatment or an intermediate treatment before requiring a total joint replacement. An example of the cartilage prosthetic implant is described for a knee joint replacement and is divided into a proximal implant configured to replace a cartilage at a distal end of a femur bone and a distal implant configured to replace a cartilage on a proximal end of a tibia bone.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
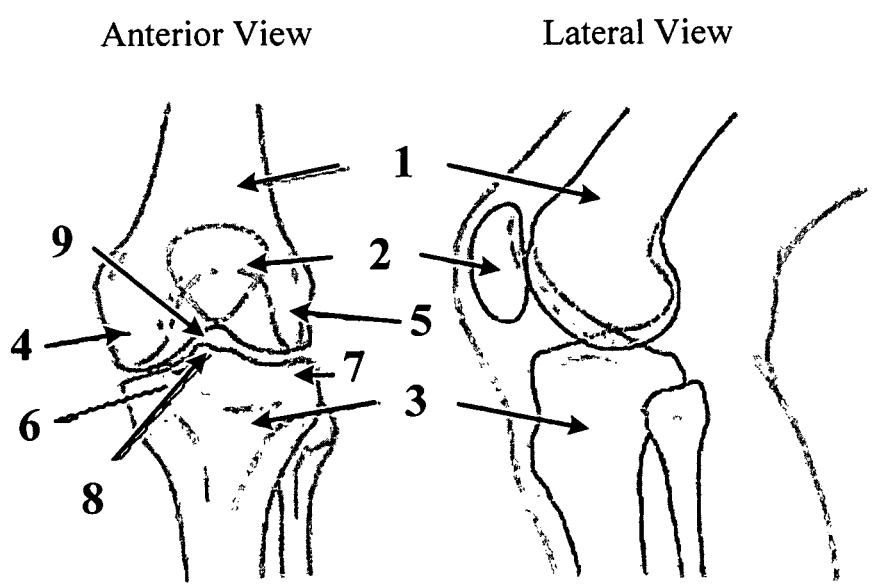
FIG. 1 illustrates a native or normal shape of a knee joint with corresponding bones from anterior and lateral views.

This disclosure relates to a cartilage prosthetic implant that can be used in orthopedics for a replacement of a damaged cartilage in a joint between a pair of bones, for example in a subject's knee in the case of osteoarthritis or trauma. The pair of bones of the joint can be labeled relative to the joint, such as a proximal bone that is proximal or above to the joint and a distal bone that is distal or below to the joint; however, other orientations, classifying, and labeling may be used. The cartilage prosthetic implant disclosed herein can be used in orthopedics, specifically in arthroplasty, by an orthopedic surgeon to replace a damaged cartilage in a joint such as in the knee joint secondary to osteoarthritis or a trauma. An articular cartilage or a cartilage is a type of tissue that is found in joints between bones and that cover both ends of the bones. The cartilage is strong and elastic, but not stiff in a normal joint, and has a smooth surface for a comfortable movement at the joint. However, once the cartilage is damaged, the cartilage's surface will lose smoothness and over time the cartilage will be lost completely. A damaged cartilage will lead to a friction between interfacing bones ends resulting in a severe joint pain with a movement, as well as a restriction of a range of motions of the joint.

A treatment of osteoarthritis in the knee joint depends on a severity of the cartilage lost and usually starts with a physiotherapy treatment and a pain relieving medication. When the damaged cartilage is great, the joint pain becomes severe and a treatment by a surgical joint replacement is done. Available methods for the surgical joint replacement include either a total joint replacement or a partial joint replacement. The partial joint replacement has gained a great interest due to requiring a small surgical incision and resulting in a fast recovery process after a surgery in comparison to the total joint replacement. In case of either the total or partial joint replacement, the damaged cartilage and a part of bone is cut and replaced by a prosthetic implant. In some occasions, the prosthetic implant will need to be removed and another one inserted either due to a damage or an infection.

An aim of a prosthetic implant is to repair or to replace a damaged body part and to restore the body part's lost functions without causing a collateral damage. However, a shortcoming in current prosthetic implants for joints is that a part of a bone needs to be cut to insert the prosthetic implant resulting in a change of a native or normal shape of the joint. As a consequence of cutting the part of the bone, the part of the bone near to the prosthetic implant will weaken the joint and make the bone vulnerable to a fracture, which may lead to complications.

A cartilage prosthetic implant is disclosed to address the shortcoming in the current prosthetic implants, whereby, instead of cutting the bone in the joint, only the cartilage will be removed on both ends of each bone in the joint and the cartilage prosthetic implant will be inserted. As a result, a risk of a bone fracture near the cartilage prosthetic implant and corresponding complications will be reduced or eliminated. The cartilage prosthetic implant is designed to maintain or restore a native joint anatomy, allowing for a natural movement at the joint. The cartilage prosthetic implant can be used as a permanent treatment or an intermediate treatment before requiring a total joint replacement.

An example of the cartilage prosthetic implant configured for a replacement of a cartilage in a knee joint is described herein; however, the cartilage prosthetic implant can modified and applied for other joints such as hip and shoulder joints. The cartilage prosthetic implant that is described for a knee joint repair is divided into a proximal implant configured to replace a cartilage at a distal end of a femur bone and a distal implant configured to replace a cartilage on a proximal end of a tibia bone. The cartilage prosthetic implant is preferably designed to resemble a shape of a normal cartilage, as well as to perform a same function as in the native or normal shape of the joint for a stability of the cartilage prosthetic implant.

The cartilage prosthetic implant can be made from materials that are commonly used in other prosthetic implants which are biocompatible with a human tissue, but may also include other materials that can further include a coating to insulate a non-biocompatible material from contacting a body tissue. The cartilage prosthetic implant can be made from materials that are commonly used for joint replacements such as metallic materials including Titanium and Chrome-cobalt-Molybdenum alloy, plastic materials including High Molecular Weight Polyethylene, and composite materials. The materials identified herein are used as examples and are not meant to be exclusive.

The cartilage prosthetic implant described herein has several advantages. The cartilage prosthetic implant can replace only the cartilage at the joint without cutting the bones. The cartilage prosthetic implant is designed to maintain or to restore the normal joint anatomy for a natural movement at the joint. While currently available prosthetic implants become loose leading to complications, the cartilage prosthetic implant described here, fixed to the bone by screws, has a greater stability and reduces a likelihood of a complication. Another advantage of the cartilage prosthetic implant described here is that a surgical procedure to implant the cartilage prosthetic implant will require a shortened surgery duration and therefore decrease an associated surgical cost as well as a risk to a patient under a prolonged anesthesia.

Referring now to the drawings, wherein like reference numerals designate identical or corresponding parts throughout the several views.

FIG. 1 illustrates a native or normal shape of a knee joint with corresponding bones from anterior and lateral views. The following descriptions of anatomical locations will help describe respective parts of the cartilage prosthetic implant that will replace a damaged cartilage in the knee joint of a subject. The cartilage prosthetic implant is configured to replace a cartilage native in a distal femur 1 and a cartilage native in a proximal part of a tibia or proximal tibia 3. The distal femur 1 has two femoral condyles in the knee joint, a medial condyle 4 and a lateral condyle 5, which are parallel to each other and are convex in shape. The femoral condyles articulate with two respective native menisci, a medial meniscus 6 and a lateral meniscus 7, referred to as the menisci.

The proximal tibia 3 has a proximal end with a non-uniform concaved surface, which can be described having two small elevations, referred to here as a tibial spine 8, in between the menisci. The tibial spine 8 is not covered by an articular cartilage. The tibial spine 8 gives the proximal tibia 3 an articulating surface with a concave shape on both sides defining the medial meniscus 6 and the lateral meniscus 7. A concave surface of the medial meniscus 6 articulates with a convex surface of the medial condyle 4, and a concave surface of the lateral meniscus 7 articulates with a convex surface of the lateral condyle 5.

Shapes of cartilages at the knee joint form structures that provide a stability of the cartilage prosthetic implant while allowing for a movement at the knee joint. When the knee joint is bent and straightened back, for example during walking, the femoral condyles will slide back and forth on the menisci and the tibial spine 8 will occupy an intercondylar fossa 9.

Figure 2A:
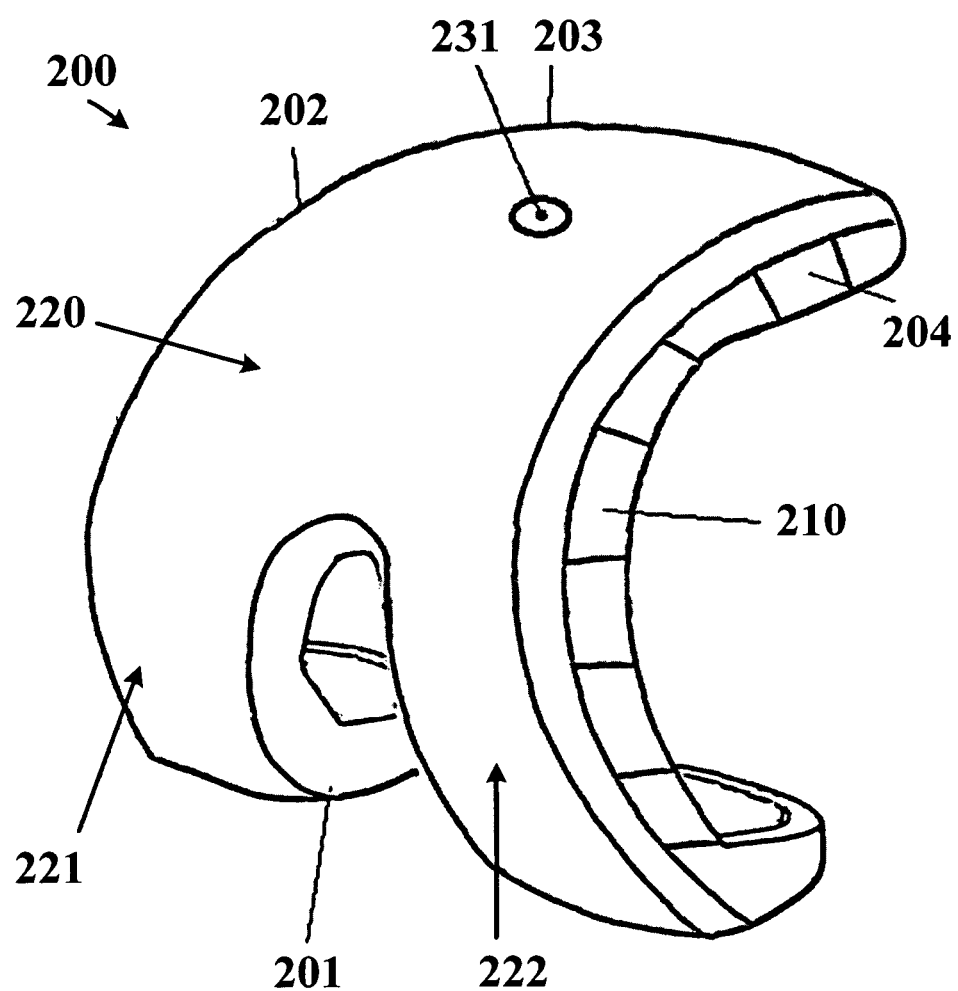
FIG. 2A illustrates a proximal implant from a frontal view according to an example.

FIG. 2A illustrates a shape of a proximal implant 200 from a frontal view. In this example, the femur bone is considered a proximal bone and the tibia bone is considered a distal bone to the knee joint. Only the cartilage in the distal femur 1 is replaced by the proximal implant 200. The proximal implant 200 is divided into two parts or portions. The proximal implant 200 has a first portion or an lower part 210 having a concave and an arched shape. The lower part 210 will be later attached to the distal femur 1. The proximal implant 200 further has a second portion or an upper part 220 contacting with the distal implant. The upper part 220 has a curvature 202 and a curvature 203 at two different areas and dimensions. The lower part 210 and the upper part 220 can be attached together and fixed to the femur bone by one or more screws.

According to an example, the lower part 210 is preferably made from a metallic material such as Titanium, but can also be any other suitable material that is used in the prosthetic implants. The upper part 220 is preferably made from a plastic material such as Ultra High Molecular Weight Polyethylene, but can also be any other suitable material. The upper part 220 can be fixed to an underlying bone by the screws. In addition, other materials can be used and the proximal implant 200 can be made from the same material for both the upper and lower parts. The proximal implant 200 can also be one part that combines one or more aspects of the upper part 220 and the lower part 210.

The cartilage prosthetic implant preferably will take a shape of a normal or native articulating cartilage on bones in a joint. In the example for the knee joint, a portion of the proximal implant 200 that covers the femoral condyles will preferably be convex in shape as shown at 222 and 221. A section 204 of the proximal implant 200 is located between the femoral condyles and the intercondylar fossa 9, and will have a concave shape of a normal knee cartilage to accommodate the distal implant and to allow for a patella bone 2 to slide smoothly, thereby improving a movement at the knee joint.

Figure 3A:
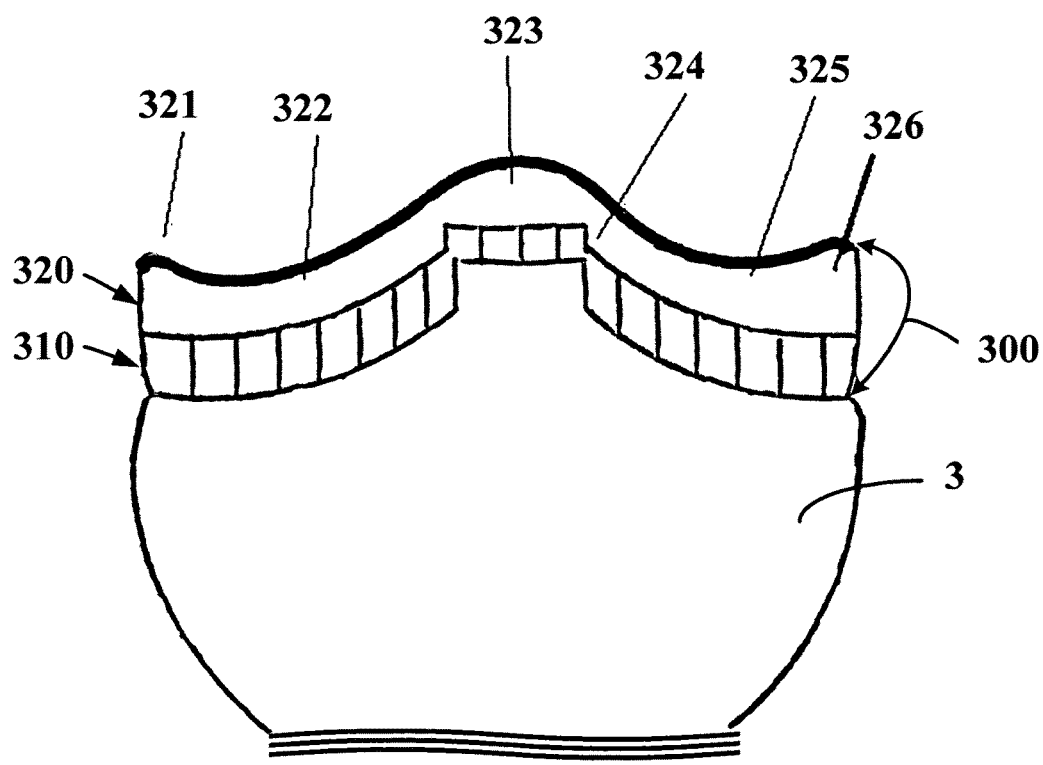
FIG. 3A illustrates a posterior view of a cross-section in a coronal plane of a distal implant attached to an underlying bone according to an example.

As shown in FIG. 3A, an example of a distal implant 300 is configured to take a shape of the menisci and to cover the proximal tibia 3. After implantation, the proximal implant 200 will slide smoothly back and forth over the distal implant 300 inside the knee joint.

As illustrated in FIG. 2A, a cleft at 201 divides a portion of the proximal implant 200 into a medial condyle section 222 and a lateral condyle section 221. The medial condyle section 222 replaces a damaged cartilage and covers a native medial femoral condyle of the distal femur 1. The lateral condyle section 221 replaces a damaged cartilage and covers a native lateral femoral condyle of the distal femur 1. The medial condyle section 222 and the lateral condyle section 221 articulate with the distal implant 300.

Figure 2B:
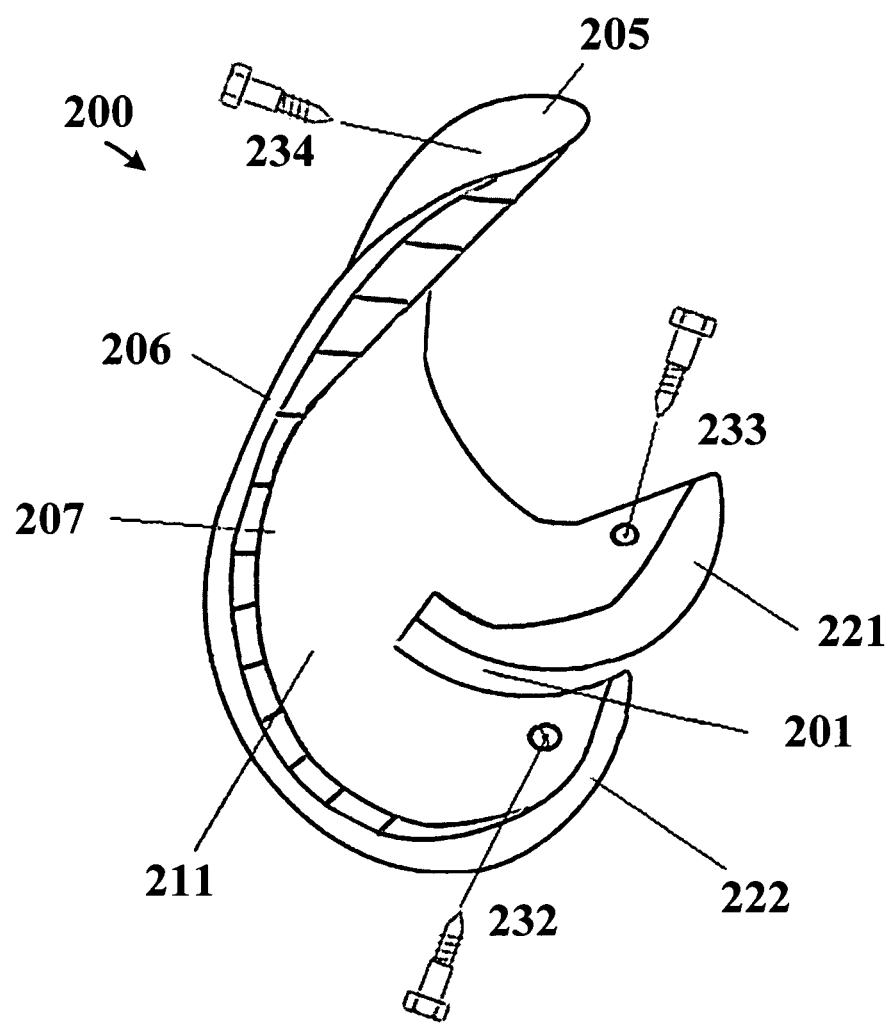
FIG. 2B illustrates a perspective view of the proximal implant showing the proximal implant's inner shape and surface according to an example.

A fixation area is an area where the cartilage prosthetic implant is preferably fixed to the underlying bone. The fixation area can have an opening through a part of the cartilage prosthetic implant and a fixation can be done by use of screws. The screws are preferably made of a biocompatible cement material, but can be any suitable material. The proximal implant 200 can fixate to the distal femur 1 by use of three screws. A first screw can secure a fixation area 231 located in an area between the native medial femoral condyle and the native lateral femoral condyle. A second screw and a third screw are shown in FIG. 2B at their respective fixation areas 232 and 233. These are just one example for the fixation areas of the proximal implant 200 and other fixation areas may be considered. A small protector piece can be placed at a fixation area to cover one or more screws.

The small protector piece can be made of a plastic or any other suitable material. The small protector piece can also be formed from a compound that is initially non-hardened and applied to the fixation area, after which it becomes hardened by a variety of means.

Figure 2C:
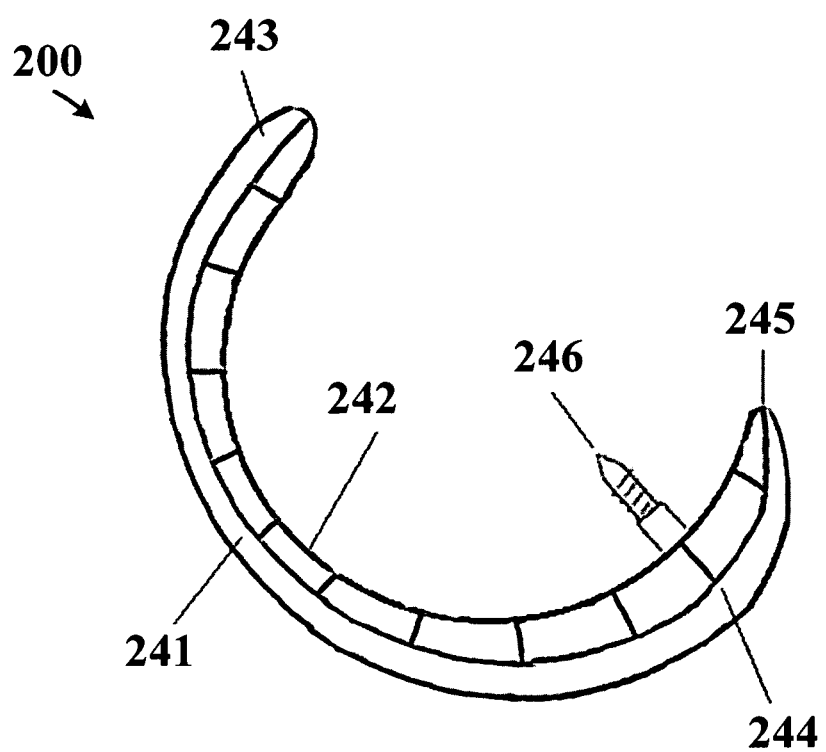
FIG. 2C illustrates a side view of a cross-section of the proximal implant according to an example.
Figure 2D:
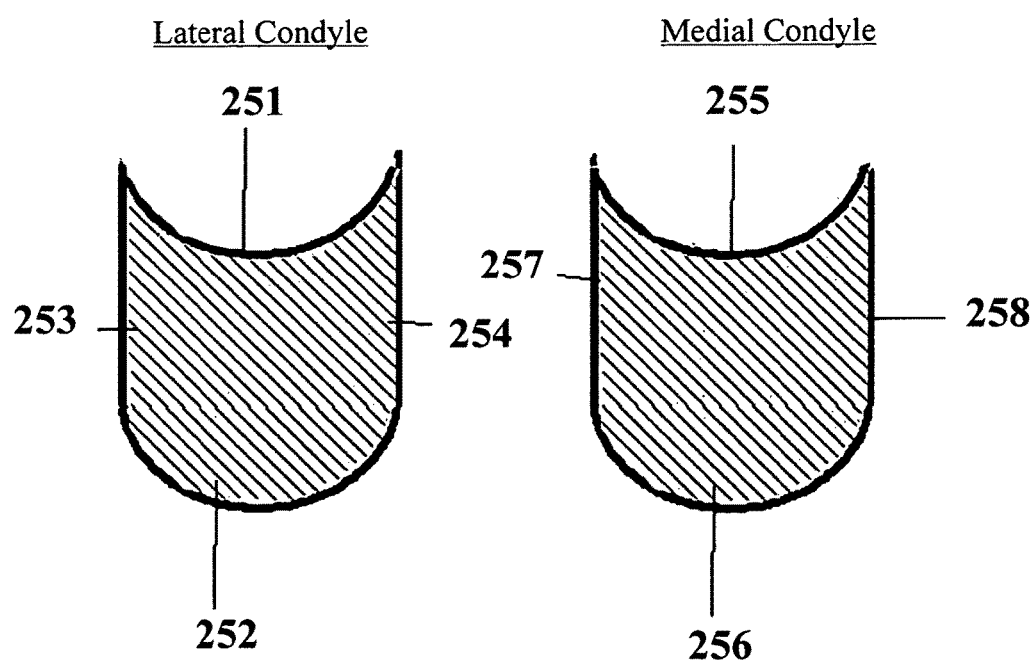
FIG. 2D illustrates a posterior view of a cross-section through the proximal implant according to an example.

FIG. 2B illustrates a perspective view of the proximal implant showing the proximal implant's inner shape and surface as an example. The proximal implant 200 preferably has an inner surface 211 that is smooth and curved, as also illustrated in FIG. 2C and FIG. 2D.

A fixation area 234 and the fixation areas 232 and 233 indicate openings through the proximal implant 200 where the screws fix the proximal implant 200 to the distal femur 1 bone.

A view of a cleft 201 is shown dividing the proximal implant 200 into the medial condyle section 222 and the lateral condyle section 221, which cover the femoral condyles of the distal femur 1 bone.

A different view of the medial condyle section 222 is shown from an anterior having a convex shape and from a posterior having a concave shape. A concave surface of the medial condyle section 222 will be in direct contact with the underlying bone. Similarly, a different view of the lateral condyle section 221 is shown from the anterior having the convex shape and from the posterior having the concave shape. A concave surface of the lateral condyle section 221 will be in direct contact with the underlying bone. FIG. 2D further illustrates inner concave surfaces of the femoral condyles.

The upper part 220 of the proximal implant 200 is illustrated having a border 205 that is curved to take a shape of the normal cartilage. An outer surface of the proximal implant 200 is illustrated having a curved shape 206. An inner surface of the proximal implant 200 is illustrated having a curved edge 207.

FIG. 2C illustrates a side view of a cross-section of the proximal implant 200 having an anterior surface and an posterior surface, as well as a relative thickness for the lower part 210 and the upper part 220. The proximal implant 200 is shown having an anterior curvature 241 and a posterior curvature 242. An end section 243 of the proximal implant 200 is configured to interface with the distal femur 1. The end section 243 is illustrated having a curvature and a relative thickness. An end section 244 of the proximal implant 200 is configured to interface with the femoral condyles. The end section 244 is illustrated with an anterior curvature, a posterior curvature, and a relative thickness. The cartilage prosthetic implant has a shape such as a curvature 245 that is similar to a native curvature of the underlying bone. A screw 246 is protruding from the proximal implant 200 to illustrate how the screw may be fixed to the underlying bone. A straight protrusion of a screw can penetrate the underlying bone. Other directions and methods may also be considered.

FIG. 2D is a posterior view of a cross-section through the proximal implant 200 at the lateral condyle section 221 and the medial condyle section 222. A proximal surface of a cross-section of the lateral condyle section 221 has a concave curved shape 251 that interfaces with the distal femur 1. A distal surface of the cross-section of the lateral condyle section 221 has a convex curved shape 252 which articulates with the distal implant 300. The lateral condyle section 221 can have an outer border shape 253 and an inner border shape 254 according to an example.

A distal surface of a cross-section of the medial condyle section 222 has a convex curved shape 256 which articulates with the distal implant 300. A proximal surface of a cross-section of the medial condyle section 222 has a concave curved shape 255 which interfaces with the distal femur 1. The medial condyle section 222 can have an outer border shape 257 and an inner border shape 258 according to an example.

Furthermore, FIG. 2D illustrates that a width of the cleft 201, as well as a width of the lateral condyle section 221 and a width of the medial condyle section 222, are preferably equal.

FIG. 3A is a posterior view of a cross-section in a coronal plane of the distal implant 300 in place of a cartilage forming a tibial plateau on the proximal tibia 3. The distal implant 300 has a shape similar to the tibial plateau. In this example, only single cartilage in the proximal tibia 3 such as the tibial plateau will be replaced by the distal implant 300. The distal implant 300 can have a similar division as the proximal implant 200, in which the proximal implant 200 is divided into two parts or portions. The distal implant 300 can have a first portion or a lower part 310 configured to be attached to the proximal tibia 3, and a second portion or an upper part 320 configured to be in contact with the upper part 220 of the proximal implant 200. The lower part 310 can be fixed to an underlying tibia bone by one or more screws (not shown).

The lower part 310 is preferably made from a metallic material, but can be any suitable material. The upper part 320 is preferably made of a plastic material, but can be any suitable material. In addition, other materials can be used and the distal implant 300 can be made from the same material for both the upper part 320 and the lower part 310. The distal implant 300 can also be made into one part that combines one or more aspects of the upper part 320 and the lower part 310.

The distal implant 300 will have a complementary surface to accommodate the proximal implant 200. The upper part 320 of the distal implant 300 has a medial meniscus section 325 and a lateral meniscus section 322. The medial meniscus section 325 and the lateral meniscus section 322 each have a concave shape configured to complement and to interface with the medial condyle section 222 and the lateral condyle section 221 of the proximal implant 200 respectively. The lateral meniscus section 322 of the distal implant 300 will articulate with the convex curved shape 252 of the lateral condyle section 221 of the proximal implant 200. The medial meniscus section 325 of the distal implant 300 will articulate with the convex curved shape 256 of the medial condyle section 222 of the proximal implant 200.

The upper part 320 of the distal implant 300 has a pair of outer borders 321 and 326 forming an elevated shape, as compared to the medial meniscus section 325 and the lateral meniscus section 322. The pair of outer borders 321 and 326 are configured to accommodate each curved or round shape of the medial condyle section 222 and the lateral condyle section 221 of the proximal implant 200 respectively.

A tibial spine section 323 is illustrated as a small elevation in a center of the distal implant 300. In addition, the lower part 310 is shown at 324 having a smaller thickness and a smaller width, as compared to the upper part 320 of the distal implant 300.

Figure 3B:
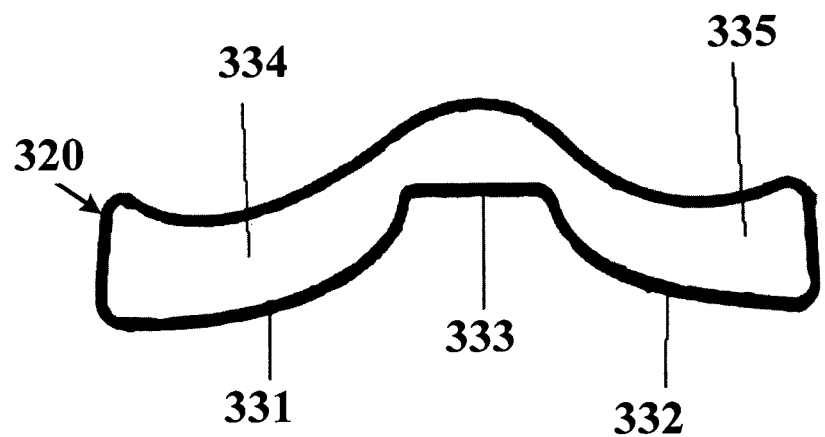
FIG. 3B illustrates a posterior view of a cross-section in the coronal plane of an upper part of the distal implant according to an example.

FIG. 3B is a posterior view of a cross-section in a coronal plane of the upper part 320 of the distal implant 300. An inferior side of the upper part 320 at the tibial spine section 323 has a flat shape 333. An inferior side of the upper part 320 at the medial meniscus section 325 and the lateral meniscus section 322 has a convex shape at 331 and 332 respectively. The upper part 320 has a similar thickness at a portion 335, corresponding with the medial meniscus section 325, and at a portion 334, corresponding with the lateral meniscus section 322.

Figure 3C:
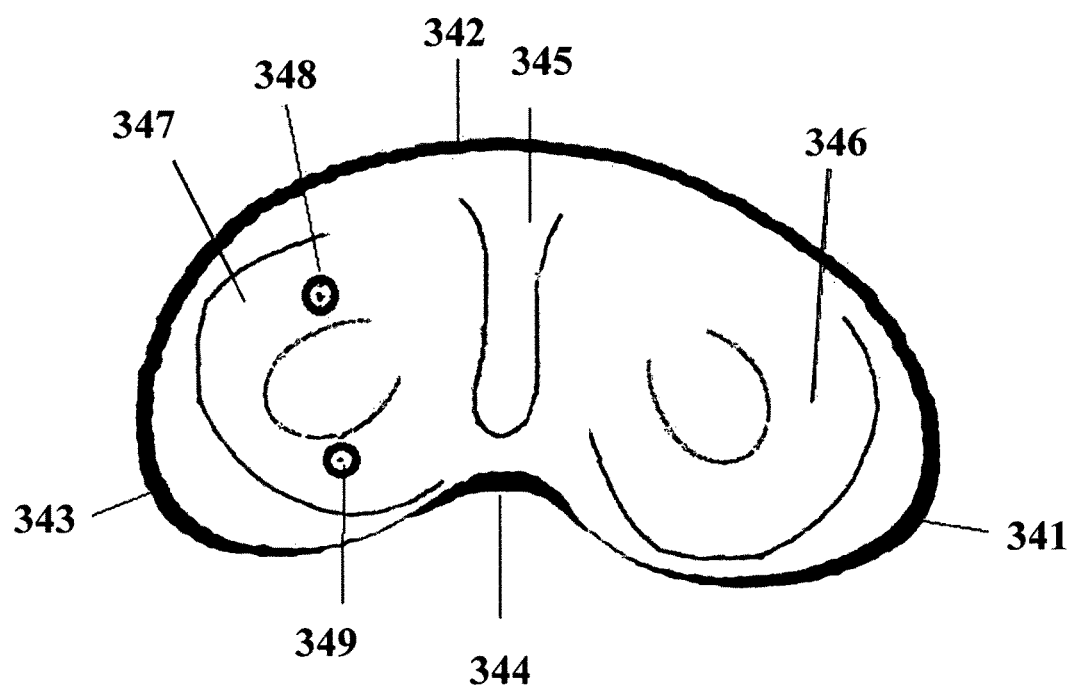
FIG. 3C illustrates an upper view in a horizontal plane of an upper part of the distal implant according to an example.

FIG. 3C illustrates an upper view in a horizontal plane of the upper part 320 of the distal implant 300. A top view of the medial meniscus section 325 and a top view of the lateral meniscus section 322 are shown at 346 and 347 respectively. The distal implant 300 has several outer borders 341, 342, 343, and 344, each outer border having a different curved shape. The outer border 344 illustrates a posterior side of the distal implant 300, which has a concave shape towards an inner side of the cartilage prosthetic implant. The outer border 342 illustrates an anterior side of the distal implant 300 having a curved shape. An outline at 345 illustrates a small elevation forming a shape of the tibial spine section 323 in the center of the distal implant 300.

The lower part 310 can be fixed to the underlying bone with at least one fixation area in each of the anterior side, the posterior side, and both the medial condyle section 222 and the lateral condyle section 221. The at least one fixation area is within the medial meniscus 346 and the lateral meniscus 347. The fixation areas 348 and 349 are shown in the lateral meniscus 347 for the anterior side and the posterior side respectively. Similar fixation areas in the medial meniscus 346 can be included (not pictured).

During a repair surgery of a damaged cartilage with the cartilage prosthetic implant, an orthopedic surgeon can make a smaller incision in comparison to an incision for a total knee replacement surgery. Further, the cartilage prosthetic implant can be inserted after a complete removal of the damaged cartilage and a remaining normal cartilage according to an example.

Obviously, numerous modifications and variations of the present invention are possible in light of the above teachings. It is therefore to be understood that within the scope of the appended claims, the invention may be practiced otherwise than as specifically described herein.

The invention claimed is:

1. A prosthetic implant assembly, comprising:
a proximal implant having a first portion and a second portion configured to replace a cartilage of a proximal bone in a diarthrodial joint, wherein the proximal implant is fixed to the proximal bone via one or more screws at one or more fixation areas; and
a distal implant having a first portion and a second a portion configured to replace a cartilage of a distal bone in the diarthrodial joint, wherein the distal implant is fixed to the distal bone via one or more screws at one or more fixation areas,
wherein at least one of the one or more fixation areas is an area of an articular surface of the prosthetic implant assembly,
wherein a surface of the first portion of the proximal implant is configured for direct contact with a distal portion of the proximal bone, the proximal bone being non-osteotomized bone,
wherein a surface of the first portion of the distal implant is configured for direct contact with a proximal portion of the distal bone, the distal bone being non-osteotomized bone,
wherein the second portion of the proximal implant has a first curvature and a second curvature and is configured to be in contact with the distal implant, the distal implant configured to be in contact with the proximal implant via the second portion of the distal implant,
wherein the first portion of the proximal implant is configured to be coupled to the second portion of the proximal implant via the one or more screws at the one or more fixation areas,
wherein the first portion of the distal implant is configured to be coupled to the second portion of the distal implant via the one or more screws at the one or more fixation areas,
wherein the one or more fixation areas have a corresponding one or more through holes, the prosthetic implant assembly being fixed to a bone via one or more screws inserted through the corresponding one or more through holes of the one or more fixation areas,
wherein one of the one or more fixation areas of the proximal implant is an articular surface of a medial femoral condyle,
wherein one of the one or more fixation areas of the proximal implant is an articular surface of a lateral femoral condyle, and
wherein a superficial portion of each of the one or more screws inserted through the corresponding one or more through holes of the one or more fixation areas is exposed.

2. The prosthetic implant assembly of claim 1, wherein the first portion of the proximal implant is made from titanium and the second portion of the proximal implant is made from ultra-high molecular weight polyethylene.

3. The prosthetic implant assembly of claim 1, wherein the first portion of the distal implant is made from titanium and the second portion of the distal implant is made from ultra-high molecular weight polyethylene.

4. The prosthetic implant assembly of claim 1, wherein the diarthrodial joint is a knee joint, the proximal bone being a femur bone and the distal bone being a tibia bone.

5. The prosthetic implant assembly of claim 4, wherein the proximal implant has a shape of the medial femoral condyle and the lateral femoral condyle of the femur bone.

6. The prosthetic implant assembly of claim 4, wherein the distal implant has a shape of a tibial plateau of the tibia bone.

* * * * *